(12) United States Patent
Leonard

(10) Patent No.: US 7,900,503 B2
(45) Date of Patent: Mar. 8, 2011

(54) METHOD OF HIGH THROUGHPUT VISCOMETRY

(76) Inventor: William Keith Leonard, River Falls, WI (US)

( * ) Notice: Subject to any disclaimer, the term of this patent is extended or adjusted under 35 U.S.C. 154(b) by 440 days.

(21) Appl. No.: 12/122,676

(22) Filed: May 17, 2008

(65) Prior Publication Data

US 2009/0282901 A1  Nov. 19, 2009

(51) Int. Cl.
*G01N 11/02* (2006.01)
(52) U.S. Cl. ....................................................... 73/54.01
(58) Field of Classification Search .................. 73/54.01, 73/54.02, 54.05, 54.13, 61.48, 61.61, 54.08
See application file for complete search history.

(56) References Cited

U.S. PATENT DOCUMENTS

| | | | |
|---|---|---|---|
| 6,393,898 B1 | 5/2002 | Hajduk | |
| 6,484,566 B1 * | 11/2002 | Shin et al. | 73/54.07 |
| 6,564,618 B2 * | 5/2003 | Shin et al. | 73/54.07 |
| 6,941,797 B2 * | 9/2005 | Nowak | 73/54.07 |
| 7,051,581 B2 | 5/2006 | Mansky | |
| 2004/0025572 A1 * | 2/2004 | Nowak | 73/54.05 |
| 2008/0014589 A1 * | 1/2008 | Link et al. | 435/6 |
| 2008/0083268 A1 * | 4/2008 | Hammami et al. | 73/54.01 |
| 2008/0190178 A1 * | 8/2008 | Hammami et al. | 73/54.01 |
| 2008/0276722 A1 * | 11/2008 | Wiedmann et al. | 73/861 |

* cited by examiner

*Primary Examiner* — John Fitzgerald
(74) *Attorney, Agent, or Firm* — Skinner and Associates

(57) ABSTRACT

An apparatus and method for measuring or comparing rheological properties of fluid samples in parallel is disclosed. The apparatus includes a plurality of sensing elements which are comprised of flow channels and reservoirs in fluid communication. The channels provide flow paths for the fluid samples which are initially contained within external reservoirs. The method includes flowing the fluid samples at variable rates and monitoring simultaneously sample flow rates from the reservoirs through a plurality elements for one or more increments of time. The disclosed method is capable of measuring or comparing rheological properties of at least two fluid samples simultaneously. Useful flow rates monitoring devices include optical array sensors and image analysis systems.

15 Claims, 3 Drawing Sheets

METHOD OF HIGH THROUGHPUT VISCOMETRY

BACKGROUND

1. Technical Field

The present invention relates to a device and technique for measuring or comparing rheological properties and viscosity of multiple samples simultaneously for rapidly screening, characterizing and comparing a library of material samples.

2. Discussion

Combinatorial chemistry generally refers to methods and materials for creating collections of diverse materials or compounds or mixtures commonly known as libraries. Additionally, it refers to techniques and instruments for evaluating or screening libraries for desirable properties. Combinatorial chemistry has revolutionized the process of formulating of mixtures and has enabled researchers to rapidly discover and optimize useful mixtures of materials.

One useful screening criterion is a liquid flow properties. Viscosity is one such property which is a physical property that characterizes a fluid's resistance to flow. For laminar flow of Newtonian fluids, including gases and simple liquids, viscosity is proportional to the tangential component of stress divided by the local velocity gradient. Complex fluids such as pastes, slurries, and polymer solutions do not follow a constant relationship between tangential stress and local velocity gradient. For them rate dependent viscosity, its analogs and other rheological measurements can serve as useful screening criteria.

Rheology is the study of the deformation and flow of fluids under the influence of an applied stress. Stress includes, for example, a shear stress, compressive stress, and extensional stress. The experimental characterization of a material's Theological behaviour is known as rheometry, although the term rheology is frequently used synonomously with rheometry. Experimentalists often refer to the measurement of rheologic properties as quantification of the movement of flowable materials in response to applied stresses. A stress is a force applied over an area.

Combinatorial libraries routinely comprise thousands of individual library members. As a result, most viscometers are unsuitable for screening purposes because they were designed to slowly process one sample at a time. Although generally the throughput of serial measurement techniques can benefit from automation, many viscometers have relatively long response times. These instruments often require time-consuming sample preparation making them impractical for use as screening tools.

U.S. Pat. No. 6,393,898 teaches simultaneously measuring viscosity of multiple samples by timing the flow of each through a sample tube of known dimensions. While this has utility it does not allow the measurement of time dependent rheological properties. It does not allow the acquisition of rheological data at two or more levels of applied stress or the testing of a property multiple times during withdrawal from a sample reservoir. This teaching does not allow visualization and quantification of complex flow patterns.

The present invention overcomes these problems noted above.

SUMMARY OF THE INVENTION

The present invention provides a method and an apparatus for measuring rheology of fluid samples in parallel using multiple elements. In some embodiments, the element apparatus includes a plurality of flow circuits each in fluid communication with a reservoir. The flow circuits include a tube and a cavity. Each tube has a length and an inner diameter. In addition, the tube provides a flow path for the fluid sample from the reservoir. The apparatus also includes a mechanism for applying a pressure differential to each element to cause the liquid to flow, and a device for monitoring flow of the fluid sample in the element.

The disclosed apparatus is capable of measuring viscosity or rheology characteristics of at least two fluid samples simultaneously. A rheological characteristic is an observable or measurable response to stress. It includes, but is not limited to a flow pattern, a rate of flow, a rate for filling a cavity, a rate of filling of a circuit, a time to move a sample volume, a rate of change of filling processes, and a rate of change of a flow process.

The present invention includes an apparatus comprised of an array of flow elements for measuring viscosity or rheological properties of fluid samples in parallel. Each of the flow elements includes a cavity where the filling may be sensed optically or with electromagnetic radiation by a detector. A single detector monitors all cavities simultaneously. The detector and its image grabbing and analysis hardware and software monitors filling in each cavity. The fill and rate of fill of a cavity are two measurements used to determine rheological characteristics of the liquids.

The method and apparatus optically samples (observes) filling of the cavity flow element at a high sampling rate allowing measurement of rheological properties many times during the short time required to remove a liquid sample from its reservoir. The high rate optical sampling of the flow in the cavity allows the measurement or comparison of time dependent rheological properties or characteristics.

When the applied pressure force is varied during the measurement time period, the high rate optical sampling of the flow in the cavity allows the rheological measurement or comparison at differing stress levels.

The present invention includes a method of screening fluid samples for differences in rheology. The method comprises (1) providing fluid samples to a plurality of reservoirs; (2) allowing the fluid samples to flow from the reservoirs through a plurality flow elements; and (3) detecting differences in the volumetric flow rates of at least two fluids simultaneously. The fill and rate of fill of a cavity are used to compare rheological characteristics of the fluids.

DETAILED DESCRIPTION OF THE PREFERRED EMBODIMENTS

Overview of a Parallel Element Viscometer

Figure 1:
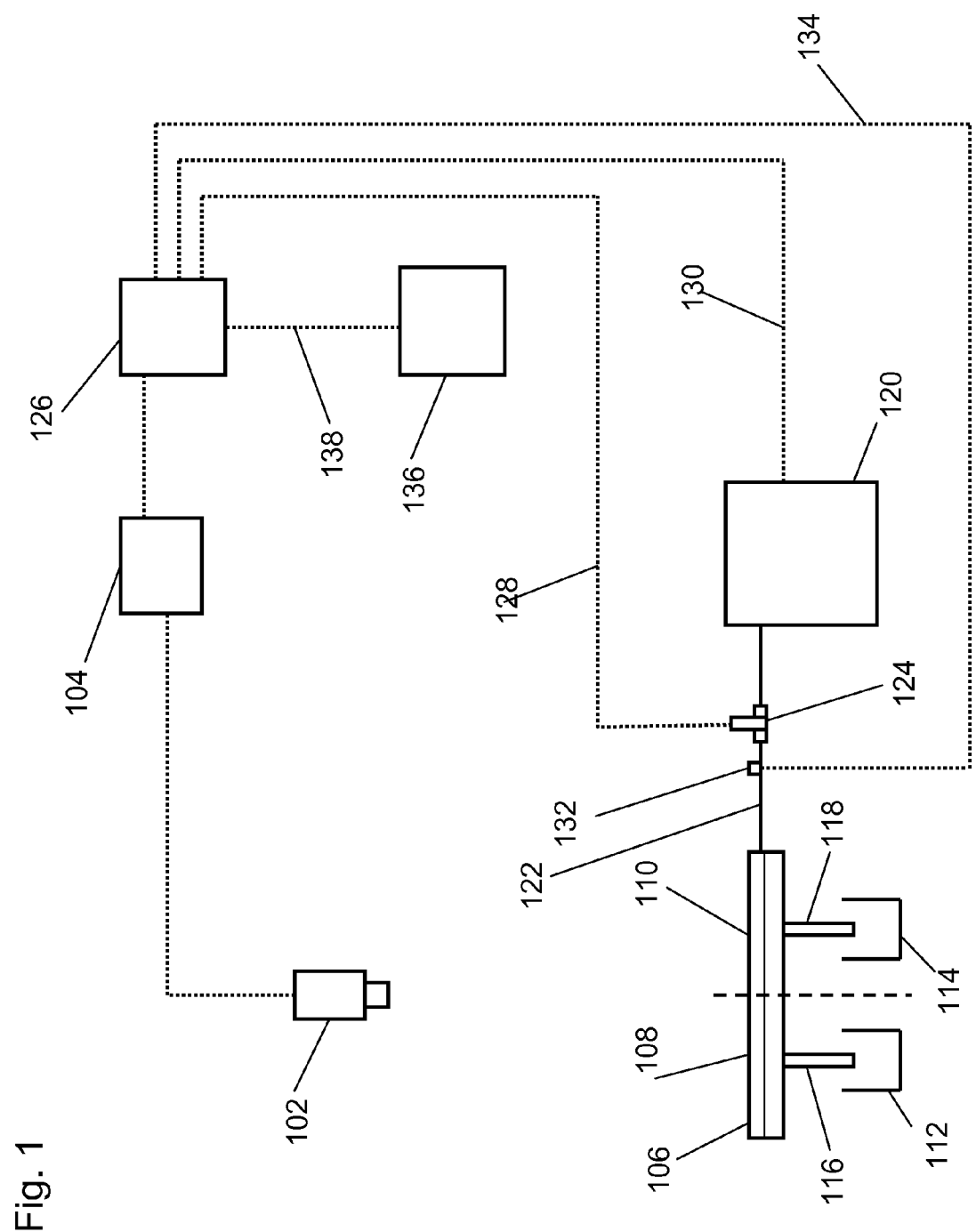
FIG. 1 is a schematic of a two element parallel viscometer apparatus that can measure or compare viscosity of two samples simultaneously.

A parallel multi-element viscometer made in accordance with the present invention generally includes two or more flow circuit elements. The flow circuits can be constructed of any material or combinations of materials including, but not limited to, metal, glass and plastic. Each of the flow circuits has a resistance to flow over its length, a rheology or viscosity measurement region, and an optical sensing region. Typically, these circuits are identical in the element. They commonly include a tube and a cavity.

One can vary the inner dimensions of individual circuit components to tune the element set design for a particular range of viscosities or rheological characteristics. In addition, the inner dimensions of the circuits may assume any value necessary to product the desired flow response. The flow may be laminar or turbulent flow if a relative measurement of a flow property is desired. From a practical standpoint, wetted volumes are minimized to allow measurements using a small sample volume. This is often the case when screening combinatorial libraries because the amount of any particular sample or library member can be as small as about 0.1 milliliters.

The multi-element viscometer includes reservoirs for holding the liquid samples prior to their introduction into the flow circuits. The reservoirs should be chemically inert with respect to the fluid samples. As noted below, it is often desirable to monitor the volumetric flow rate through the tubes by detecting changes in sample volume flowing from the reservoir. Since optical techniques are well suited for this task, flow circuits include a cavity with see-through wall which allows a portion of the circuits to be monitored optically. This is referred to as the detection cavity or cavity.

The parallel viscometer also includes an optical imaging capturing device for monitoring the degree and rate of fill of the detection cavity. The volumetric flow rate of the samples flowing through the circuits may be calculated from the images. Once the volumetric flow rate is known, one may calculate the viscosity of the samples as the fluid viscosity is related to the volumetric flow rate and the pressure drop across the viscosity measurement region of an individual element. The parallel element viscometer includes a mechanism for applying and monitoring a pressure differential that drives the liquid samples through the elements. Typically, the parallel viscometer employs a pressure reservoir to supply the pressure differential driving the liquid through the elements Useful devices for monitoring the volumetric flow rate include in general electromagnetic radiation imaging sensors that monitor the flow elements simultaneously. The sensor may comprise a light source and an image grabber device, which generates a digital image of the degree of fill of a cavity in each element as a function of time. If a simple tube is connected to the sensing cavity, the time interval for a known volume of sample to pass through the viscosity measurement region (the tube) allows calculation of viscosity. The parallel viscometer typically uses an image data acquisition device in tandem with a computer and necessary software to record the sensor output. The data acquired is used to determine flow rate as a function of time. In its very simplest form the frame grabber device is a digital camera which is used to take multiple photos of the flow progressing through the cavity portion of the element with a see through wall. If the flow channels in each element have the same flow resistance, comparisons of the images of the first and the second elements allows determination of a difference in apparent viscosity between the two fluids.

When a simple tube is connected to the optical cavity, the apparent viscosity is calculated from the tube diameter, the flow rate, and the pressure differential from the inlet to the outlet of the tube.

When complex or non-Newtonian fluids are tested, rheological similarities or differences may be determined by comparing the degree of fill of the cavities, rate of fill of cavities or flow patterns as a function of time.

Details of a Two Element Parallel Rheometer

FIG. 1 shows a schematic of a two element parallel rheometer system that can measure viscosity or rheology of two samples simultaneously. The rheometer includes an optical image grabbing device 102 connected to an electronic image processing device 104. The image grabber 102 looks at a compound viscosity measuring plate assemble 106 consisting of two individual measurement flow channel elements 108 and 110.

The assembly 106 samples fluid from reservoirs 112 and 114. The physical flow path connections to the reservoirs are provided by tubes 116 and 118.

The movement of fluid through the measurement assembly 106 is powered by an air pressure tank 120. The pressure in this tank may be positive or negative relative to the air above the reservoirs 112 and 114. It may be controlled and changed during the duration of the rheology test. The assembly 106 is connected to the pressure tank 120 by process pipe 122 and three way valve 124. The valve 124 is electronically control by a data acquisition and process controller 126 through signal communication line 128. The pressure in the tank 120 is supplied and controlled by a system not shown. This will commonly be an air compressor or a vacuum pump. Pressure in the tank is measured by a sensor not shown which sends a signal to the process controller 126 by way of signal communication line 130.

Device 132 measures the air pressure into the element assembly 106 and sends a signal to the data acquisition and process controller 126 by way of line 134.

Imaging processing device 104 converts the image signal grabbed by device 102 and converts it into an array of digital data for further processing by the data acquisition and process control system 126. The imaging processing device 104 controls the image grabber and the timing of the acquisition of multiple images of the assembly 106. The grabber 102 may be a two dimensional array device such as exemplified by a digital camera.

The data acquisition and process control system 126 is capable of receiving and sending digital and analog signals. It is capable of processing signals and sending digitalized data to computer 136. It is capable of responding to data calculated by the computer 136. Communication is through communication line 138.

Figure 2:
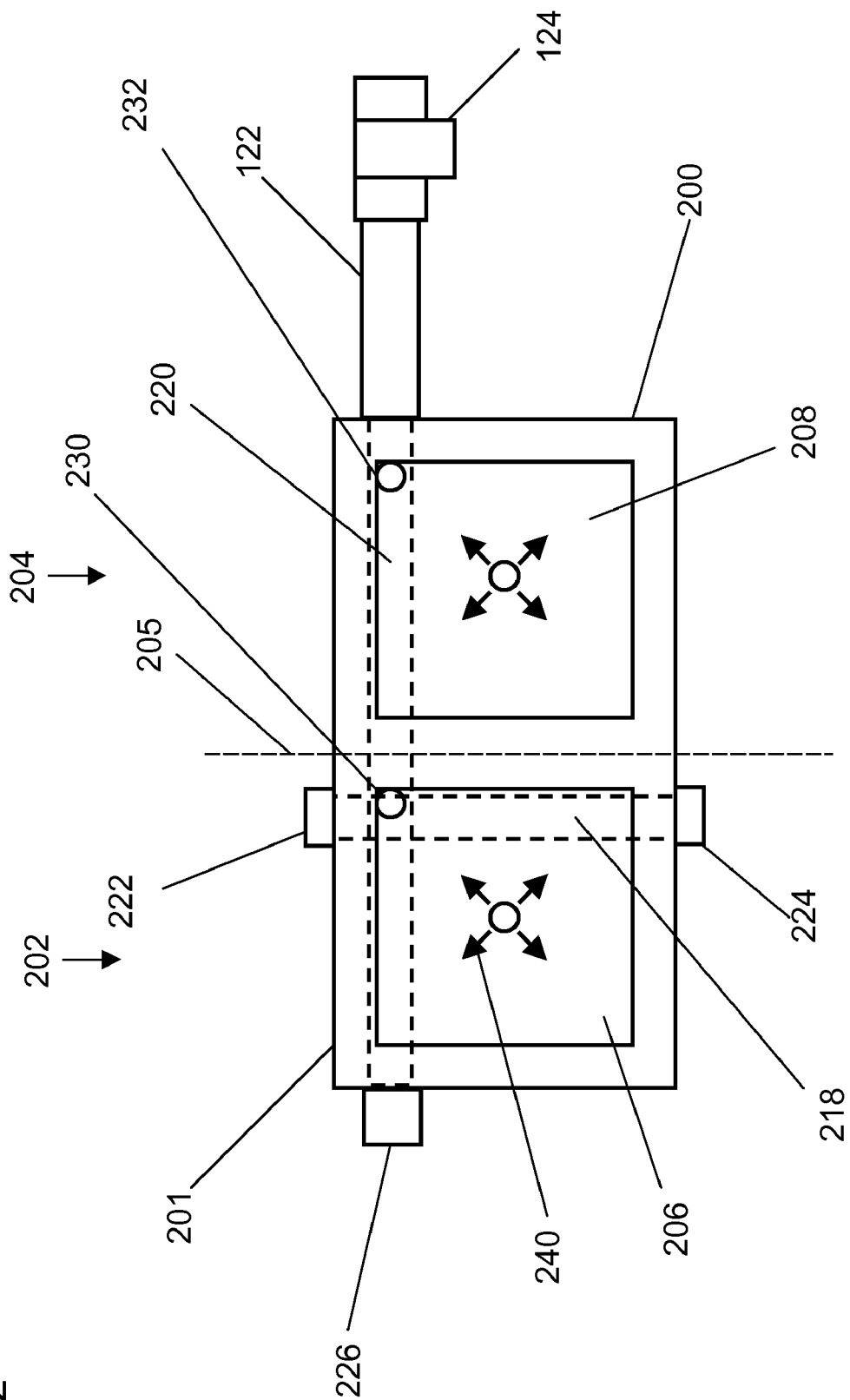
FIG. 2 shows a top view of a two element flow assembly.
Figure 3:
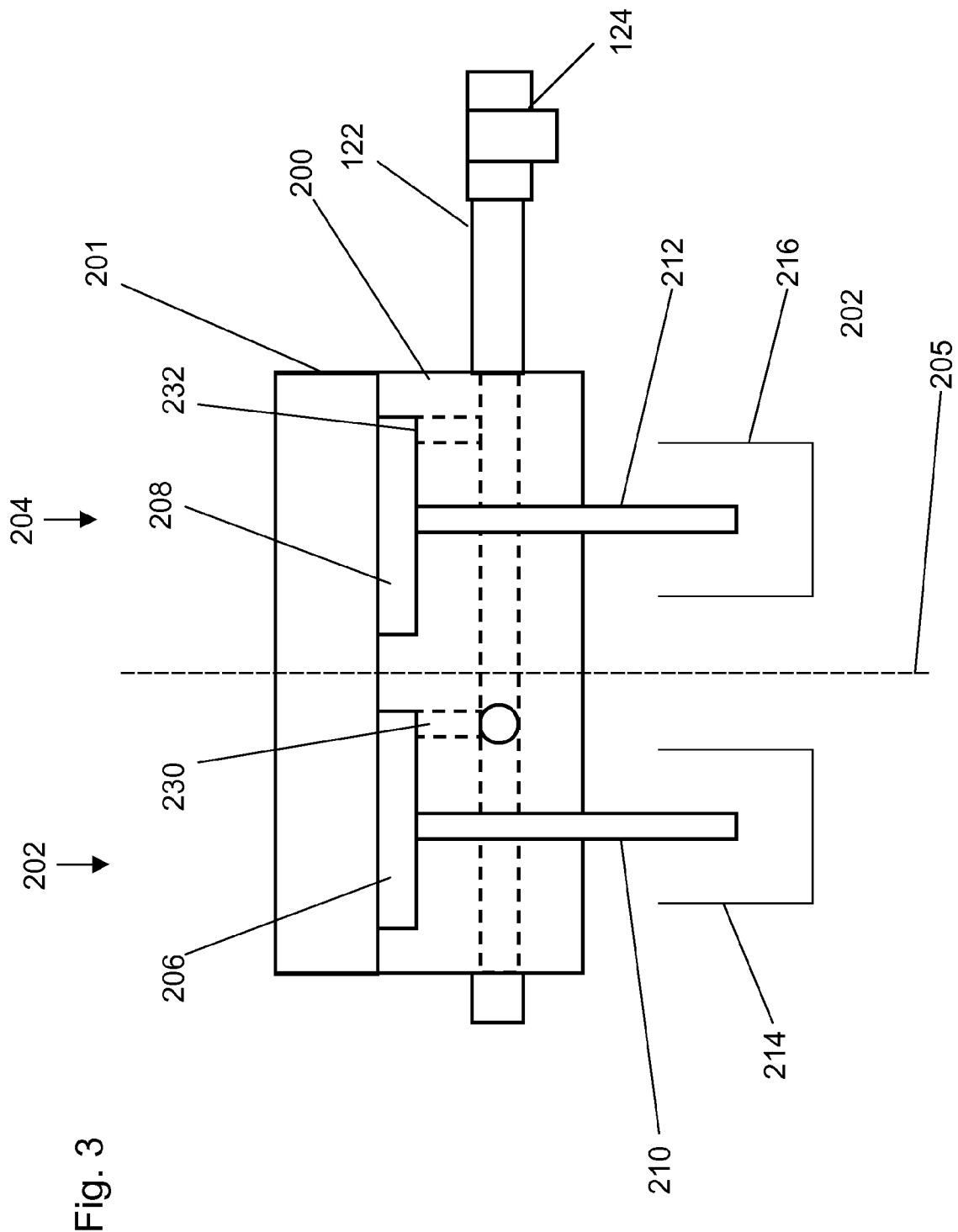
FIG. 3 shows a cross sectional view of a two element flow assembly.

Referring to both FIGS. 2 and 3 simultaneously, FIG. 2 shows a detail top view of a two element flow assembly 106, and FIG. 3 shows a cross sectional view of this assembly 106. The assembly contains the flow circuits.

It consists of a main block 200 and an optical cover 201. Block 200 includes two elements 202 and 204 which are positioned to the left and right of the dashed line 205 respectively. These two elements are both machined into the same base block 200. The two elements include a cavities 206 and 208, flow tubes 210 and 212, and fluid reservoirs 214 and 216. Flow tubes 210 and 212 connect fluid reservoirs 214 and 216 to cavities 206 and 208 respectively.

In main base block 200 are two air passageways 218 and 220 which extend horizontally through the block. Passageway 218 is blocked at both ends by plugs 222 and 224 and may be used if the assembly is coupled to other assemblies (not shown) to construct a compound assemble of more than two viscometers.

Passageway 220 is blocked at one end by plug 226, and connects at the other end to flow pipe 122. Vertical holes 230 and 232 connect passageway 220 to cavities 206 and 208 respectively.

To operate the viscometer the reservoirs 214 and 216 are placed under block 200 so that the tubes 210 and 212 are submerged in the two fluids to be tested. Then a suction pressure is applied through pipe 122. Threeway valve 124 is activated to allow a negative gage pressure to be applied to passageways 218 and 220. Negative pressure in passageway 220 is transmitted through vertical holes 230 and 232, cavities 206 and 208, and tubes 210 and 212. This pressure forces fluid from the reservoirs and into the tubes 210 and 212.

The measurement of the flow resistance in the first element 202 takes place in its flow channels 210 and 206. More specifically, flow is observed in cavity 206. As fluid enters the cavity a liquid-air interface is created. The flow radiates outward as indicated by the arrows 240 and the position of the interface changes with time.

The interface is normally visible to the naked eye, a camera or an image grabbing optical device. One such device may be a digital camera commonly used for photography. Industrial frame grabbing inspection devices are also widely available, and these interface with digital image processors and high speed image storage devices all of which can down load data to a computer for analysis.

Usually, the differing optical properties of the liquid versus the air it is displacing in cavity 206 allows the differentiation of the liquid and air filled areas in cavity 206. This is especially true if the liquid is opaque. Therefore, one is able to monitor the degree of fill of the cavity 206 as time proceeds. The degree of fill is a prime response variable and will vary with the liquid rheology, the geometry of the internal channels 206 and 210, and the air pressure applied through pipe 122.

Viscoelastic liquids and non-Newtonian fluids commonly exhibit flow path patterns distinctly different from Newtonian fluids. It is a teaching of this invention to capture and quantify these with the imaging system.

A. Comparison Flow Testing with a Single Element

The liquid flow paths in element 202 have a liquid flow resistance which is a function of the flowing fluid rheology. Because of this the degree of fill of cavity 206 with time will be a function of rheology of the fluid being tested. Different rheology of fluids tested in element 202 will result in different fill versus time data if the applied pressure through pipe 122 is the same. Therefore, sequential testing of liquid samples through element 202 can determine if they have different rheologies.

B. Comparison Flow Testing with Two or More Elements

If the elements 202 and 204 resist liquid flow equally for identical liquids then differences in rheology of two different liquids may be detected by observing the filling characteristics such as the amount of fill as a function of time of cavities 206 and 208. Likewise, if the flow paths are unequal but calibrated relative to each other using a standard fluid, then differences in rheology of two liquids may be detected by observing the filling characteristics such as the amount of fill as a function of time of cavities 206 and 208. In a similar manner the simultaneous testing of more than two liquid samples may be carried out simultaneously using a number of elements simultaneously as long as they have identical or calibrated resistances to the flow of liquids through them.

C. Design of the Liquid Flow Channels

Design of the liquid flow channels offers multiple possibilities with respect to the steady flow rheological characteristics one may measure or compare. The process time scale, the accuracy desired, the cost of fabrication on an element, and many other factors may be adjusted. The geometry of the channels 210 and 206 offers many possibilities.

As shown in the FIGS. 2 and 3 and described above, channel 210 is a tube, and pressure driven tube flow regime dominates the fluid dynamics if the entrance and exit region effects are small in comparison to the flow in the tube. However if the tube length flow resistance is small relative to the entrance and exit resistances the converging flow into the tube entrance or the diverging flow out of the tube into the cavity may dominate the flow resistance. If this is the case, rheological properties other than shear viscosity may be investigated for liquids especially non-Newtonian liquids. Converging and diverging flows react to the elongational flow rheology of fluids. Examples of such fluids where this may be important are solutions of long chain polymers. Many commercially used solution thickening agents produce quite pronounced elongational flow resistance.

As shown in the FIGS. 2 and 3, the liquid flows from tube 210 into cavity 206 and proceeds radially outward in a slot. This axisymetric radial flow can be used for non-Newtonian liquids to investigate rheological properties other than simple shear viscosity.

D. Design for Time Dependent Flow Testing

The design of the viscometer allows comparative testing of time dependent flow properties of liquids. The pressure applied by to the elements by pipe 122 may be varied with time. Since the optical sensing of the filling of cavities can be recorded as a function of time, their filling rates can be compared under transient conditions. Transient filling rates in response to step changes in applied pressure can be used to compare time dependent rheology of liquid samples.

E. Design for Shear Dependent Flow Testing

The design of the viscometer allows comparative testing of shear rate dependent flow properties of liquids. The pressure applied to the elements by pipe 122 may be varied with time. The pressure differential driving the flow through tube 210 and its companions may be ramped up with time producing higher and higher tube flow shear rates. Since the optical sensing of the filling of cavities can be recorded as a function of time, their filling rates or degree of fill can be compared at different times during the filling process and related to different tube flow shear rates.

F. General Extensions of the Method

Two or more cavities may be connected in series or parallel may be provided in a single viscometer element. This may be used to provide redundant measurements. This may be also used to provide measurements at two or more flow rates.

Those skilled in the art of fluid flow will recognize that the flow resistances of liquid contacting flow channels and their entrances and exits may be changed by altering their dimensions or geometry. This can make a particular resistance large and dominant relative to the others.

The cavity geometry may be changed to create a cavity where the cross section geometry is that of a constant width and height slot. The cavity may be made with a varying height. The cavity may have a height that varies with the distance from the entrance so that the observed surface area does not vary linearly with the volume of fill. The cavity may be a tortuous narrow channel which follows a path that wraps back on itself. The cavity channel path may be a spiral.

Those skilled in the art of fluid flow or rheometry will recognize many other geometry variations of the element flow circuits are possible all of these are within the scope of the invention.

What is claimed is:

1. A method for sensing at least one rheological characteristic of a fluid sample comprising the steps of:
   a) providing at least one assembly including:
      i) a means for holding a fluid sample;
      ii) a fluid flow element providing a flow path for said fluid sample, said fluid flow element having channels terminating at a first end adapted for removing said fluid sample from said holding means; and
      iii) at least one sensing element for said fluid sample in said fluid flow element with a wall transparent to electromagnetic radiation;

b) providing a means for flowing a portion of said fluid sample into said sensing element;
c) providing a means for illuminating said sensing element with electromagnetic radiation;
d) providing a means of capturing at least one image of said sensing element using said electromagnetic radiation;
e) flowing said fluid sample out of said holding means;
f) flowing said fluid sample into said sensing element;
g) capturing at least one image of said sensing element; and
h) sensing the at least one rheological characteristic.

2. A method of claim 1 wherein four or more assemblies are provided.

3. A method of claim 1 wherein said sensing step includes measuring the degree of fill of said sensing element.

4. A method of claim 1 wherein said sensing step includes recording a flow pattern in said sensing element.

5. A method of claim 1 wherein two or more said sensing elements exist in parallel.

6. A method of claim 1 wherein two or more said sensing elements exist in series.

7. A method of claim 1 wherein said sensing step includes calculating a rheologic response using said image.

8. A method of claim 1 wherein said image is a digitalized image.

9. A method for sensing at least one rheological characteristic of two or more fluid samples comprising the steps of:
   a) providing for each fluid sample an assembly including:
      i) a means for holding a fluid sample;
      ii) a fluid flow element providing a flow path for said fluid sample, said fluid flow element having channels terminating at a first end adapted for removing said fluid sample from said holding means; and
      iii) at least one sensing element for said fluid sample in said fluid flow element with a wall transparent to electromagnetic radiation;
   b) providing in each said assembly, a means for flowing a portion of said fluid sample into said sensing element
   c) providing a means for illuminating said sensing element of each said assembly with electromagnetic radiation;
   d) providing a means of capturing at least one image of said sensing element in each said assembly using said electromagnetic radiation;
   e) flowing said fluid sample out of said means for holding in each said assembly;
   f) flowing said fluid sample into said sensing element in each said assembly;
   g) capturing at least one image which includes all said sensing channels; and
   h) sensing at least one rheological characteristic for each said assembly.

10. A method of claim 9 wherein two or more said sensing elements exist in parallel in said assemblies.

11. A method of claim 9 wherein two or more said sensing elements exist in series in said assemblies.

12. An apparatus for sensing at least one rheological characteristic of a fluid sample comprising:
   a) at least one assembly including:
      i) a means for holding a fluid sample;
      ii) a fluid flow element providing a flow path for said fluid sample, said fluid flow element having channels terminating at a first end adapted for removing said fluid sample from said holding means; and
      iv) at least one sensing element for said fluid sample in said fluid flow element with a wall transparent to electromagnetic radiation;
   b) a means of capturing at least one image of said sensing element using electromagnetic radiation; and
   c) a means of sensing at least one rheological characteristic.

13. An apparatus of claim 12 further including a means for flowing a portion of said fluid sample into said sensing element.

14. An apparatus of claim 12 further including a means for illuminating said sensing element with said electromagnetic radiation.

15. An apparatus of claim 1 wherein said means of capturing at least one image is a digital image and processing system.

* * * * *